United States Patent [19]

Enstrom

[11] Patent Number: 4,676,244

[45] Date of Patent: Jun. 30, 1987

[54] MEDICAL LANCET

[76] Inventor: Hans Enstrom, Graners Grand 1, S-151 57 Sodertalje, Sweden

[21] Appl. No.: 541,989

[22] Filed: Oct. 14, 1983

Related U.S. Application Data

[63] Continuation-in-part of Ser. No. 245,080, Mar. 18, 1981, abandoned.

[30] Foreign Application Priority Data

Apr. 23, 1980 [SE] Sweden .................. 8003057

[51] Int. Cl.⁴ ............................................ A61B 17/32
[52] U.S. Cl. .................................................. 128/314
[58] Field of Search .................. 128/329 R, 330, 314, 128/315; 604/156, 157, 144

[56] References Cited

U.S. PATENT DOCUMENTS

| | | | |
|---|---|---|---|
| 2,442,416 | 6/1948 | Kulicke et al. | 128/314 |
| 3,358,689 | 12/1967 | Higgins | 128/329 R |
| 3,815,604 | 6/1974 | O'Malley et al. | 128/305 |
| 4,164,224 | 8/1979 | Hastings | 128/330 |

FOREIGN PATENT DOCUMENTS

| | | | |
|---|---|---|---|
| 188439 | 1/1957 | Austria | 128/314 |
| 2074453 | 11/1981 | United Kingdom | 128/314 |

Primary Examiner—Michael H. Thaler
Attorney, Agent, or Firm—Murray Schaffer

[57] ABSTRACT

A plunger having an oblong body with a front end and a rear end and a lancet having a pointed end section projecting axially from said body at the front end is insertable in a cylinder having an oblong hollow body with a front end, a rear end and an axial hole. The plunger of such a length and the lancet is so arranged that the pointed end section of the lancet protrudes a predetermined distance out of the cylinder at the front end when the plunger is inserted thereby defining an operative puncturing position of the medical lancet. The plunger and cylinder have a first engaging stop arranged after partial insertion of the plunger, to temporarily prevent continued insertion at a predetermined initial position. The arresting function of the stop is overcome by applying pressure on the plunger thereby pushing it the remaining distance into the cylinder from the initial position to the operative position.

5 Claims, 6 Drawing Figures

MEDICAL LANCET

RELATED APPLICATION

This patent application is a continuation-in-part of co-pending Ser. No. 245,080 filed 3/18/81, now abandoned.

BACKGROUND OF THE INVENTION

The present invention relates to an improved medical lancet means for effecting bleeding by puncturing skin of an individual to permit collecting a drop of blood for diagnostic purposes or the like medical use.

It is known to puncture the skin with a lancet retaining body which is used in combination with a separate mechanical apparatus including a biased striker mechanism and a device to release said striker. The striker mechanism has a support for mounting a lancet retaining body therein. Such an apparatus is expensive in manufacture and time-consuming in use. When the lancet is mounted in the support there is the danger of the sterile lancet being accidently touched with the fingers or other objects with consequent danger of bacterial contamination of the lancet. Neither is it possible to make the lancet tip invisible for the patient.

It is, therefore, an object of the present invention to provide an improved medical lancet means which can be produced more economically and which can be used more conveniently and safely than previously designed lancets.

It is a further object of the present invention to provide a medical lancet means which does not require packaging in a separate wrapper in order to insure the sterility thereof and which makes use of all members thereof for the incision including the member that protects the lancet tip.

These and other objects of this invention will become apparent from the detailed description and the claims to follow when read in conjunction with the accompanying drawing.

DESCRIPTION OF THE INVENTION

Figure 1:
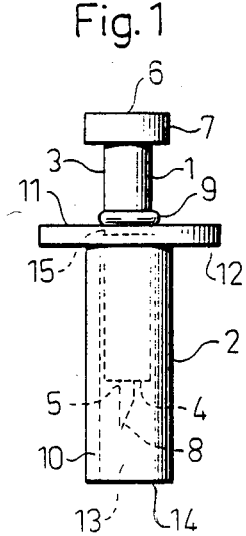
FIG. 1 is a side view of a medical lancet means according to one embodiment of the invention in initial position.

The improved medical lancet means shown in the drawings comprises two cooperating members in the form of a male member 1 and a female member 2 both of which preferably being disposable.

The male member comprises an oblong solid, cylindrical rod body 3 and a lancet 5 of suitable metal projecting axially from the front end 4 of the rod body. It also comprises a circular pressure plate 7 formed at the rear end 6 of the rod body. The rod body and the pressure plate are manufactured of suitable plastic material in one piece, the lancet being moulded into the body at the same time so that it is permanently fixed in the solid rod body and so that a pointed end section 8 thereof projects axially therefrom. Furthermore, the male member 1 carrying the lancet is provided with a circumferential ridge 9 or the like protrusion to temporarily obstruct movement, or some other temporary stop means, the function of which will be explained below.

The female member acting as carrier and guide for the male member comprises an oblong, sleeve-like, open-ended, cylindrical hollow body 10 and a finger-grip plate 12 formed at the rear end 11 of the body.

In the embodiment shown, the body 10 has an axial through hole 13 adapted to slidingly receive the rod body 3 of the male member without friction. A slight clearance may be permitted between the parts.

The male and female members are so designed with respect to each other that when the male member is fully inserted in the female member the pointed end section 8 of the lancet will project a predetermined distance, usually about 0.5-2 mm, out of the female member. In this final and puncturing operative position the pressure plate 7 is in contact with the finger-grip plate 12 or rear end 11. The female member is manufactured of of suitable plastic material, preferably of the same plastic material as the male member.

Figure 2:
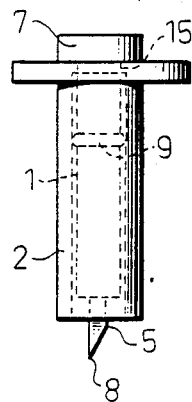
FIG. 2 is a side view of the means according to FIG. 1 in operative position when in use.

The medical lancet means also comprises first engaging stop means adapted to constrict passage or temporarily obstruct movement, said stop means comprising a first element arranged on the rod body of the male member at a predetermined distance from the pointed end section 8 of the lancet, and a second element arranged on the female member at a predetermined distance from the front end 14 thereof to engage with said first element. In the embodiment shown said first element consists of said radially prodruding ridge 9, while the second element consists of a corresponding annular radially inwardly extending ridge 15 on the inner wall or at the entry of the hole in the female member. The ridge 15 of the female member thus forms a constriction of the hole 13 at the entry thereof so that continued movement of the male member into the female member is prevented, as is illustrated in FIG. 1, since the ridge 9 engages the protrusion 15 of the female member. By increasing the pressure with the thumb or other finger on the pressure plate 7 of the male member, this stop is finally overcome so that the male member can be inserted the full length determined by the rod body 3 into the female member, as is illustrated in FIG. 2. When this increased pressure is suddenly released by the ridges 9, 15 moving past and out of engagement with each other, the male member acquires an extremely high speed the rest of the distance into the female member until second engaging stop means are reached. These second stop means thus comprise the pressure plate 7 of the male member and the rear end 11 of the female member. This in turn means that the pointed end section 8 of the lancet is pushed out of the female member at a corresponding high speed, rapidly penetrating the skin and the blood vessels beneath. It will be understood that the front end 14 of the female member will be in contact with the skin at least from the point when the pressure is increased on the male member after the temporary engagement of the first stop means has been reached.

Since the lancet acquires a high speed upon the sudden release and pushing in of the male member, the pointed end section of the lancet will penetrate the skin extremely quickly. It has been found that, thanks to this, the sensation of pain is extremely slight and brief.

Figure 3:
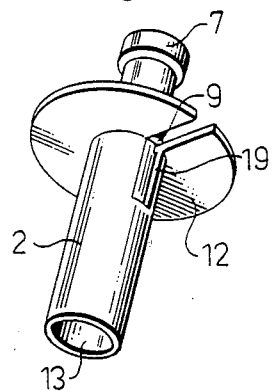
FIG. 3 is a perspective view of a modified embodiment of the means according to the invention.

The ridge 9 on the male member is placed at a specific point on the rod body 3 so that the distance between the ridge 9 and the pointed end section 8 of the lancet is the same as and preferably slightly less than the distance between the front end 14 of the female member and the stop ridge 15. It is thus ensured that the pointed end section 8 of the lancet will not be visible from the side when the first stop means is temporarily in engagement, provided the female member is made of opaque plastic, which is preferred. It is believed that it is of great psychological significance for many patients that the lancet is invisible, If desired, the female member may be provided with a slit 19 at its rear end 11, to enable the entry to the hole 13 to expand upon application of said pressure on the male member. Such an embodiment is illustrated in FIG. 3.

Figure 4:
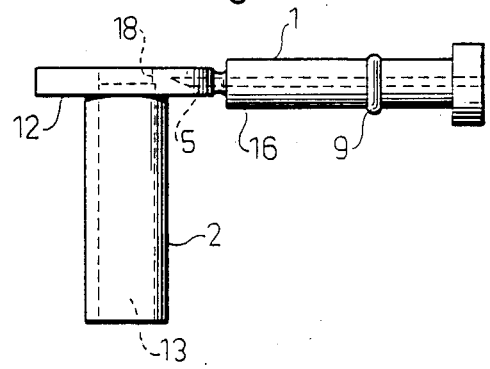
FIGS. 4 and 5 are a side view and top view, respectively of another embodiment of a means according to the invention produced as a unit with the lancet unexposed and sterile, but having members which can be separated.
Figure 5:
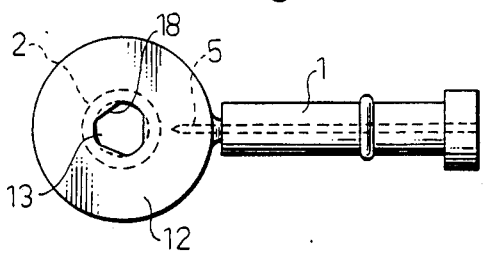

The medical lancet means can preferably be made in one piece, the male member and female member being in an integral piece or unit 16 and easily severable from each other at the moment of use. Such a unit is shown in FIGS. 4 and 5. The unit is injection moulded so that the pointed end section of the lancet is located in the finger-grip plate 12 of the female member and directed radially therein. A slight twist of the male member will separate this from the female member at the thin and frangible connection 17 which surrounds a small portion of the lancet. The lancet being moulded in this manner, it is completely protected and sterile up to the moment of use and, moreover, by an operative member, i.e. the female member, of the medical lancet means. Thus, no special protection element which must then be disposed, is required for the lancet. In the embodiment according to FIGS. 4 and 5, the female member has been provided with three evenly distributed ridges or protrusions 18 cooperating with the protrusion 9 of the male member to form said first stop means.

Instead of placing the male and female members in right angle, as shown in FIG. 4, they may be moulded to form an oblong unit, the pointed end section of the lancet being enclosed in the finger-grip plate 12 from above and, if necessary, in extra material under the plate.

The plastic material used for the medical lancet means is entirely free from foreign substances and is of a quality approved for foodstuffs. Thus, plasticized organic polymeric compositions, such as a polyvinyl chlorida, polyethylene, polypropylene and the like plastic materials, are well suited for moulding the medical lancet means. The lancet is made of special stainless steel. By means of a special technique it has been found unnecessary to provide the lancet with any grindings, such as grooves or external attachment means which are normal for the attachment of a lancet or other steel object in a plastic body. This new technique entails washing the lancet with alcohol or alcohol solution prior to its automatic insertion in the plastic injection moulding tool, without any object with fat or oily surface coming into contact with the lancet after washing.

To ensure secure accurate moulding of the lancet into the male member, the injection moulding tool may comprise three radially directed holder elements which support the automatically inserted lancet from two opposite directions, such as from below and above, corresponding radial slits being formed in the moulded male member.

The stop means which act last, i.e. said second stop means which are formed in the embodiment shown by the pressure plate 7 of the male member and the rear end 11 of the female member, according to an alternative embodiment may be formed by the front end 4 of the male member and an inner shoulder or ridge in the female member, said shoulder or ridge being formed by a bottom section in the female member, the hole thereof terminating at a distance from the front end of the female member. A narrow central hole is made in said bottom section for passage of the pointed end of the lancet.

Figure 6:
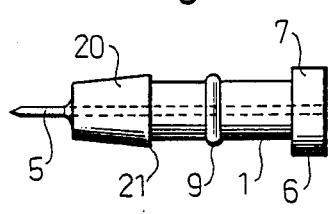
FIG. 6 is a side view of another embodiment of a plunger according to the present invention.

According to a further embodiment, shown in FIG. 6, the male member is provided with a device which prevents the male member from falling out of the female member when the medical lancet means is in its initial position prepared for use. Such a device comprises a plunger 1 which is provided with a conical forward end 20 which is enlarged on its rear so that it forms a circumferential protrusion 21. This protrusion 21 is arranged to engage with either ridge 15 or 18 of the cylinder 2 after the partial insertion of the plunger into the cylinder. The diameter of the protrusion is smaller than that of the ridge 9 but greater than the entrance of the hole 13 in order to engage with the ridge 15 or 18. Thus, the protrusion 21 forms a further stop means which prevents the plunger and lancet from accidentally falling out of the rear end of the cylinder and thereby ensures the sterility of the lancet once it has been removed from its sterile position and made ready for use. A ridge, step or similar stop means may be formed on rod body 3 between front end 4 and ridge 9 in view of a circular protrusion.

As mentioned, the lancet may consist of a suitable metal. However, it may of course consist of some other suitable material if desired. The lancet may, for instance, consist of a suitable plastic material and according to such an embodiment the lancet is moulded as an integral part of the male member, i.e. of the same plastic material.

What I claim is:

1. A disposable miniature medical lancet for obtaining a drop of blood by puncturing the skin without passing through the body comprising a cylinder and a plunger, said cylinder being distensible in the radial direction under force applied thereto, said plunger being insertable at its front end into said cylinder, said plunger and said cylinder having a slight clearance enabling said plunger to be normally freely slidable within said cylinder, said plunger having a radially extending flange at its rear end engageable with the rear end of said cylinder for limiting passage of said plunger through said cylinder and defining the full insertion of said plunger in said cylinder, lancet integrally formed with said plunger and having a pointed end projecting axially from said front end of said plunger, said plunger, cylinder and lancet being so formed that said lancet protrudes from the front end of said cylinder a predetermined distance when said plunger is fully inserted within said cylinder, the outer surface of said plunger having a radially outwardly protruding peripheral ridge spaced from the rear end thereof and the inner surface of said cylinder having at least one radial projection extending inwardly from the wall adjacent the rear end thereof, and peripheral ridge and radial projection cooperating to form detent means temporarily restricting the freely slidable movement of said plunger at a predetermined location within said cylinder, said location being less than the full insertion of said plunger so that said lancet remains within said cylinder spaced from the front end thereof, said restriction being overcome by application of an axial force on said plunger at said rear end thereof, said axial force causing said cylinder to distend in the radial direction permitting the peripheral ridge to pass axially beyond said projection without fracture of said ridge or projection, said plunger being thereafter freely movable through said cylinder rapidly into the fully inserted position. and wherein the cylinder has a slit at said rear end to enable the entrance of the cylinder to expand upon said upon said application of pressure on the plunger.

2. The lancet according to claim 1, wherein said plunger and cylinder are molded as a unit, said plunger being integrally connected at its forward end to portion of said cylinder, so as to be easily severable said connection being thin and easily frangible permitting severance of said plunger from said cylinder and exposure of the tip of said lancet.

3. A medical lancet according to claim 1 wherein the cylinder is formed with a radially exterior flange forming finger-grip for the user.

4. The lancet according to claim 1 wherein said lancet protrudes from the front end of said plunger, when fully inserted in said cylinder between 0.5-2 mm.

5. The lancet according to claim 1 wherein said projection at the rear end of the entrance to said cylinder comprises a circumferential ridge having a diameter less than that of said peripheral ridge of said plunger but greater than that of the entrance to said cylinder at the rear end.

* * * * *